United States Patent [19]

Tazi

[11] Patent Number: 4,956,430
[45] Date of Patent: Sep. 11, 1990

[54] PROCESS FOR PREPARING SUBSTANTIALLY PURE HIGH MOLECULAR WEIGHT VINYL LACTAM-QUATERNIZED ACRYLAMIDE COPOLYMERS

[75] Inventor: Mohammed Tazi, Wayne, N.J.

[73] Assignee: GAF Chemicals Corporation, Wayne, N.J.

[21] Appl. No.: 345,820

[22] Filed: May 1, 1989

[51] Int. Cl.$^5$ .............................................. C08F 2/10
[52] U.S. Cl. ..................................... 526/195; 526/89; 526/215; 526/216; 526/233; 424/81
[58] Field of Search ............... 526/227, 215, 233, 195, 526/89, 216

[56] References Cited

U.S. PATENT DOCUMENTS 3,428,617 2/1969 Sobolev ................................ 526/264
3,509,113 4/1970 Mohagle .............................. 526/264
4,456,741 6/1984 Ames ................................... 526/264
4,663,408 5/1987 Schulz ................................. 526/240

Primary Examiner—Christopher Henderson
Attorney, Agent, or Firm—Marilyn J. Maue; Joshua J. Ward

[57] ABSTRACT

The invention relates to the production of high molecular weight vinyl lactam-quaternized amino acrylamide copolymers having less than 0.1% residual unreacted monomer, which comprises: subjecting the monomers to solution polymerization in the presence of a buffering agent having chelating properties for complexing with traces of heavy metals; controlling the pH of the polymerization to a level above 5.5 while continuously ebulating nitrogen gas through the system during reaction and incrementally adding a free radical initiator in 2 to 4 stages during the conversion to copolymer. The invention also relates to the substantially pure vinyl lactam-acrylamide copolymer having a Brookfield viscosity of at least 75,000 cps. and a residual monomer content below 0.5 wt. %, for example less than 1,000 ppm.

11 Claims, No Drawings

PROCESS FOR PREPARING SUBSTANTIALLY PURE HIGH MOLECULAR WEIGHT VINYL LACTAM-QUATERNIZED ACRYLAMIDE COPOLYMERS

BACKGROUND OF THE INVENTION

Several synthetic polymers containing vinyl lactams are presently used in cosmetic and textile formulations to provide high penetration of other active components, to contribute body and holding power to hair sprays, setting lotions, etc. and to promote softening and moistening in skin and body conditioners. Most of these synthetic polymers are comprised of vinyl lactam and acrylate or methacrylate monomers as in U.S. Pat. Nos. 3,954,960 and 3,914,403. While these copolymers provide excellent hair adhesion and set hold under conditions of high humidity, they are subject to excessive hydrolysis when formulated into cosmetic formulations at a pH greater than 7 and/or maintained at a elevated temperature, for example temperatures in excess of 40° C., for considerable time. Hydrolysis causes the polymer to decompose forming an alcohol amine which can result in significant lowering of viscosity and concomitant reduction in beneficial properties.

While the polymer of U.S. Pat. No. 4,057,533 overcomes some of the above disadvantages, such polymers containing the aminomethyl acrylamide moiety of this patent are known to be unstable and to decompose to methylol amide and an ammonium salt upon heating (see U.S. Pat. No. 2,344,934) or in the presence water (Journal of the Society of Dyers and Colourists, Volume 63, page 260, 1947 by F.V. Davis and SURFACE ACTIVITY, Van Nostrand Press, 2nd Edition, 1961, page 241 by J.L. Moilliet, B. Collie and W. Black). Other processes for producing amino acrylamide lactam copolymers result in prohibitive amounts of toxic unreacted quaternized monomer which render the polymeric product unsuitable for cosmetic formulations and personal care treating applications.

Accordingly, it is an object of this invention to minimize or eliminate the process disadvantages discussed above and to provide a less contaminated product which can be employed directly in sensitive areas of application such as in cosmetic or medicinal formulations.

Another object of the invention is to provide a commercially feasible and economical method for the manufacture of high molecular weight vinyl lactam-quaternized acrylamide copolymers.

Still another object is to provide an improved copolymerization process which is carried to completion within a shortened period of time.

Still another object is to maximize the efficiency of polymerization initiators in the copolymerization of a vinyl lactam and a quaternized acrylamide.

Yet another object is to provide a high molecular weight vinyl lactam/quaternized amino acrylamide copolymer having less than 0.1 wt. % residual monomer.

These and other objects will become apparent from the following description and disclosure.

THE INVENTION

In accordance with this invention there is provided a solution copolymerization process which is effected in a oxygen-free atmosphere between a quaternized amino acrylamide monomer having the formula

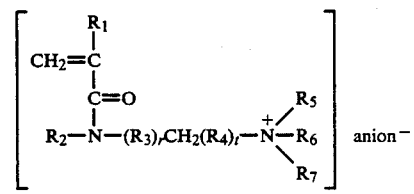

and a vinyl lactam monomer having the formula

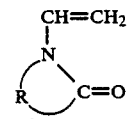

wherein R is alkylene having from 3 to 8 carbon atoms and is optionally substituted with lower alkyl; $R_1$ and $R_2$ are each independently hydrogen or methyl; $R_3$ and $R_4$ are each independently alkylene having from 1 to 18 carbon atoms which is optionally substituted with alkyl; the sum of r and t is 1 to 3; $R_5$ and $R_6$ are each independently lower alkyl; $R_7$ is hydrogen, alkyl, aralkyl or alkaryl having from 1 to 8 carbon atoms or an N-alkylene lactam radical having from 3 to 8 carbon atoms and said anion is halogen, tosylate, $SO_3$, $SO_4$, $HSO_4$, $R_7SO_4$ or other acidic anion. Of the above lactam reactants, vinyl pyrrolidone and vinyl caprolactam are preferred.

Of the quaternized amino acrylamide monomers, acrylamides and methacrylamides wherein $R_7$ is hydrogen or lower alkyl and $R_3$ and $R_4$ are each $C_1$ to $C_4$ alkylene, are preferred.

The process incorporates four essential and critical conditions, namely contacting the monomers in the presence of a buffer having chelating properties capable of complexing with trace quantities of heavy metals; controlling the pH of the reaction medium at 5.5 or higher throughout reaction with said buffering agent; adding free-radical initiator at incremental stages during the reaction and continuously purging the reaction mixture by ebullition of nitrogen gas. These essential elements are applied to the general process of contacting the monomers at a temperature of between about 30° C. and about 150° C., preferably between about 55° C. and about 75° C., for a period of from about 1 to about 10 hours, preferably from about 2 to about 5 hours, under a pressure ranging between 20 mm Hg to about 50 psi, preferably at atmospheric pressure.

The copolymerization is carried out in an aqueous solution wherein the concentration of water with respect to reactants and product is between about 50 and about 90% by weight, preferably between about 75 and about 85% by weight.

In effecting the present copolymerization, the buffering agent is introduced into the reactor as an aqueous solution, after which the monomers in the desired proportions of 85–99.5 wt. % vinyl lactam and 0.5–15 wt. % of the quaternized acrylamide are added.

The product resulting from the above described process is a copolymer containing from about 85 to about 98% by weight of the vinyl lactam copolymerized with from about 2 to about 15% by weight of the quaternized amino acrylamide comonomer, which product contains less than 0.1% by weight of unreacted monomer. Because of the high degree of purity resulting from a conversion of at least 99.9%, the substantially colorless product of this reaction, having an average molecular weight of between about $5 \times 10^4$ and $5 \times 10^6$ or a Brookfield viscosity between about 75,000 and about 250,000 cps. at 25° C., can be used directly in chemical formulations. Alternatively, the product can be concentrated by removal of water, if desired.

The present product finds wide application in formulations to provide hair and skin conditioning properties, viscosity building characteristics and to impart resistance to hydrolysis in alkaline solutions. The present copolymeric products also have excellent hair and skin substantivity so that their conditioning effects endure for extended periods. For the purposes of this discussion, the term "conditioning" is intended to include the functions of moisturizing, softening, lusterizing, body building, penetrating and others which enhance the feel and appearance of the skin or hair. The copolymers also act as dye levelling and dye retention aids. Generally, between about 0.5 and about 10 wt. % is added to a formulation to provide conditioning effects.

As described above, the buffering and chelating agent is critical in obtaining a product with low residual monomer. This agent performs a dual function in the reaction. Specifically, it complexes with traces of heavy metals introduced by the aqueous medium or by the reactor, which metals normally contaminate the product and poison the catalytic initiator. The buffering agent also controls the pH at a critical level of not less than 5.5, preferably to a level on the basic side between about 6.1 and about 10. Below a pH of 5.5, the vinyl lactam rate of polymerization is too slow to compete with the more active quaternized comonomer. Thus, when the level approaches 5.5, additional quantities of buffer are added to increase basicity. Generally, the amount of buffer employed represents between about 0.05 and 0.5 wt. %, preferably between about 0.15 and about 0.3 wt. % of the vinyl lactam monomer. Suitable agents which combine buffering and chelating activity are those which have a pH greater than 5 and include ethylene diamine tetraacid disodium salt, tetrasodium pyrophosphate, anhydrous dibasic sodium phosphate + monobasic potassium phosphate, borax, sodium carbonate + sodium bicarbonate, tribasic sodium phosphate and calcium hydroxide. These buffering agents are employed as 0.005 molar to saturated aqueous solutions at 25° C. Such buffers as ethylene diamine tetraacid and its tetrasodium salts are not suitable since they are found to leave a high ash residue and do not possess sufficient complexing capability for trace amounts of heavy metals present in the system.

The continuous or incremental addition of initiator throughout the reaction, is also essential to insure high molecular weight copolymer. It is found that repeated contact of unreacted monomers with fresh catalyst, particularly during the final stages of reaction when monomer concentration is greatly reduced, drives the reaction to completion. The gradual or incremental addition also promotes more efficient and conservative use of initiator while permitting a shorter overall reaction time which can be reduced to less than 4 hours. By employing the selected buffering agents, the initiator activity remains high throughout the copolymerization.

Suitable initiators employed in the present process are those free radicals conventionally used in solution polymerization and include t-butyl peroxy pivalate, t-amyl peroxy pivalate, di-tertiary butyl peroxide, lauroyl peroxide, decanoyl peroxide, azobisisobutyronitrile, etc. However, in cases where the copolymeric product of the invention is to be employed in cosmetic or medicinal formulations or for comestible product packaging, the use of azobisnitrile types should be avoided because of their toxic by-products.

Continuous purging of the reaction by constant ebullition of nitrogen maintains the oxygen-free atmosphere and is important in substantially removing acetone and carbon dioxide by-product while maintaining catalyst activity. A combination of all the above discussed process conditions is critical to the preparation of copolymer having a Brookfield viscosity at 25° C. of 60,000–100,000 cps and low residual toxic monomer.

Having thus generally described the invention, reference is now had to the accompanying Examples which set forth preferred embodiments but which are not to be construed as limiting to the scope of the invention as more broadly described above and in the appended claims.

EXAMPLE I

Into a nitrogen purged 30 gallon stainless steel reactor equipped with an Anchor agitator, reflux condenser and temperature control water jacket was introduced 6.75 grams of tetrasodium pyrophosphate dissolved in 250 grams of dionized water. To this solution, 13,512 grams of N-vinyl pyrrolidone and 4,769 grams of the quaternized ammonium chloride salt of dimethylaminopropyl methacrylamide was added in an aqueous mixture and nitrogen ebullition was commenced. The reactor was then heated and maintained at about 60° C. and 26.4 grams of t-butylperoxypivalate in 100 grams of water was added. The contents were stirred at 60 rpm for 1 hour, after which a second charge of 26.49 grams of t-butylperoxypivalate in 100 grams of water was added. The reaction was continued for 2 additional hours until no further generation of reaction exotherm occurred. The nitrogen purge was then discontinued and the reactor contents cooled with cooling water.

The colorless copolymeric product was recovered in aqueous solution with 99.9% conversion of monomers. The copolymer had an average molecular weight of $6 \times 10^5$ determined by gel permeation chromatography and residual monomer was below 0.1% by weight as measured by high pressure liquid chromatography.

EXAMPLE II

Example I is repeated except that N-vinyl caprolactam is substituted for N-vinyl pyrrolidone and trimethyl aminobutyl acrylamide ammonium bromide is substituted for dimethylamino propyl methacrylamide. Also the pivalate initiator is continuously added in an increasing amount during the entire course of the reaction. The conversion to the corresponding lactam-acrylamide copolymer having an average molecular weight of about $8 \times 10^5$, was 99.7%.

The product of Example I was directly incorporated into various personal care formulations.

| A. HAND AND BODY LOTION | | |
|---|---|---|
| | Ingredients | % by Weight |
| A. | Distilled Water | 51.9 |
| | Carbomer 1342 | 0.4 |
| | Glycerin | 3.5 |
| | Sorbitol | 2.0 |
| | Dimethicone | 10.0 |
| | Mineral Oil | 2.0 |

A. HAND AND BODY LOTION (continued)

| | Ingredients | % by Weight |
|---|---|---|
| B. | Triethanolamine 99% | 0.2 |
| C. | Distilled Water | 25.0 |
| | Copolymer of Example I | 5.0 |
| D. | Fragrance and Preservative | qs |

The carbomer of part A was sifted into distilled water contained in a glass mixing vessel and mixed until homogeneous, after which the remaining Phase A ingredients were added in the order listed. The carbomer was then neutralized with the 99% triethanolamine and parts C and D were added with constant mixing until a homogeneous mixture was obtained.

The formulation when applied as a hand cream and body lotion leaves the skin soft and moisturized without greasy effect, thus indicating good penetration.

B. HAIR STYLING GLAZE

| Ingredients | % by Weight |
|---|---|
| Copolymer of Example I | 10.0 |
| Olealkonium Chloride | 1.0 |
| Hydroxyethylcellulose (Natrosol 250HHR < Hercules) | 1.0 |
| Distilled Water | 87.9 |
| DMDM Hydantoin (Glydant, Glyco) | 0.1 |

In a glass mixing vessel containing distilled water at 55° C., hydroxyethylcellulose was added with constant agitation. The resulting mixture was cooled and the remaining ingredients were added at reduced mixing speed until homogeneous.

The product had an approximate pH of 5.9 and a viscosity of 6,5000 cps (Brookfield Viscometer Model RVT, Spindle #5, 10 rpm at 25° C.).

The above formulation applied to the hair after shampooing provided high luster without any damaging effect.

C. CONDITIONING AND STYLING MOUSSE

| Ingredients | % by Weight |
|---|---|
| Distilled Water | 86.2 |
| Copolymer of Example I | 4.6 |
| PVP/VA S-630 (GAF) | 0.9 |
| EMULPHOR ® ON-870 (GAF) | 0.5 |
| CHEELOX ® BF-13 (GAF) | 0.1 |
| DMDM Hydantoin | 0.2 |
| Fragrance | qs |
| n-Butane | 4.5 |
| Difluororethane | 3.0 |

The copolymer of Example I was mixed until dissolved in the distilled water contained in a glass mixing vessel after which the remaining ingredients (not the propellants) were sequentially added in the order listed. Each ingredient was agitated until dissolved before adding the next ingredient. The resulting concentrate was introduced into a suitable aerosol container and pressurized with propellants. Spraying the hair with the above formulation produced high luster and manageability.

D. CONDITIONING AND EXTRA STYLING MOUSSE

| Ingredients | % by Weight |
|---|---|
| Distilled Water | 84.3 |
| Copolymer of Example I | 4.6 |
| GAFFIX ® VC-713 (GAF) | 2.8 |
| EMULPHOR ® ON-870 (GAF) | 0.5 |
| CHEELOX ® BF-13 (GAF) | 0.1 |
| DMDM Hydantoin | 0.2 |
| Fragrance | qs |
| n-Butane | 4.5 |
| Difluoroethane | 3.0 |

The mixing procedure for this formulation is the same as that described above for C. This formulation produced the same properties as C except for stronger curl retention.

E. HAIR CONDITIONING GEL

| Ingredients | % by Weight |
|---|---|
| Distilled Water | 95.98 |
| Carbomer 1342 | 0.61 |
| Triethanolamine 99% | 0.91 |
| Copolymer of Example I | 2.50 |
| Fragrance and Preservatives | qs |

The mixing procedure for this formulation is the same as that described above for A. When applied to the hair this formulation produced a soft, lusterous texture and greatly improved combability.

F. CLEAR HAIR CONDITIONING LOTION

| | Ingredients | % by Weight |
|---|---|---|
| A. | Distilled Water (55° C.) | 50.0 |
| | Hydroxyethylcellulose | 0.5 |
| B. | Distilled Water (25° C.) | 32.5 |
| | Copolymer of Example I | 5.0 |
| C. | Lauramine Oxide | 7.5 |
| | Alcohol SD 40 | 3.0 |
| | Fragrance and Preservative | qs |
| D. | Citric Acid, 20% | |

Hydroxyethylcellulose was well mixed with water at 55° C. in a glass mixing vessel. The copolymer was mixed in a separate vessel with water until dissolved and then added with mixing to part A. The ingredients of part C were then separately added with mixing after each addition and the final pH was adjusted to 5 with citric acid. The product had a viscosity of 1000 cps, (Brookfield RVT Spindle No. 6 at 50 rpm). This conditioning formulation, when applied to the hair after shampooing provided excellent combability and eliminated frizz after hair drying.

G. CONDITIONING MOUSSE

| Ingredients | % by Weight |
|---|---|
| Distilled Water | 87.1 |
| Copolymer of Example II | 4.6 |
| EMULPHOR ® ON-870 (GAF) | 0.5 |
| CHEELOX ® BF-13 (GAF) | 0.1 |
| DMDM Hydantoin | 0.2 |
| Fragrance | qs |
| n-Butane | 4.5 |

G. CONDITIONING MOUSSE

| Ingredients | % by Weight |
| --- | --- |
| Difluoroethane | 3.0 |

The mixing procedure and results for this formulation is the same as that described in formulation C.

H. CONDITIONING SHAMPOO

| Ingredients | % by Weight |
| --- | --- |
| Distilled Water | 52.8 |
| Ammonium Lauryl Sulfate, 28% | 30.0 |
| ALKAMIDE ® CDO (GAF) | 3.5 |
| Cocamidopropyl Betaine | 5.0 |
| PEG-6000 Distearate | 2.5 |
| Copolymer of Example I | 5.0 |
| Methychloroisothiazolinone and Methylisothiazolinone | 0.1 |
| Fragrance | qs |
| Citric Acid | 0.3 |
| Ammonium Chloride | 0.8 |

The surfactants were added to the water at 70° C. in a glass mixing vessel and stirred until PEG-6000 distearate was melted, after which the mixture was cooled and the copolymer of Example I was added at 45° C. and agitated until a homogeneous mixture was obtained. Fragrance and preservative were then added and the pH of the mixture was adjusted to 5.5 with citric acid. Also the viscosity was raised to 6000 cps (Brookfield RVT; spindle No. 6 at 50 rpm) with ammonium chloride.

I. CONDITIONING SHAMPOO

| | Ingredients | % by Weight |
| --- | --- | --- |
| A. | Copolymer of Example I | 8.0 |
| B. | TEA Lauryl Sulfate (Standapol T, Henkel) | 25.0 |
| | ALKAMIDE ® CDM (Alkaril) | 5.0 |
| | Distilled Water | 61.9 |
| | Methylchloroisothiazolinone and Methylisothiazolinone (Kathon CG, Rohm & Haas) | 0.1 |

The copolymer of Example I was dissolved in 20 parts of the 61.9 parts of water. In a separate container the components of B were added to the remaining 41.9 parts of water at 70° C. and mixed. The polymer solution was then added to part B and the resulting mixture cooled to 40° C. after which preservative was added and the mixture cooled to room temperature. The product has a pH of 7.5 and a viscosity of 140 cps (Brookfield Viscometer Model RVT, spindle #4 10 rpm at 25° C.). Hair cleansed with this formulation had a silky, lusterous texture and showed no signs of frizzing.

J. PERMANENT WAVE LOTION

| | Ingredients | % by Weight |
| --- | --- | --- |
| A. | Distilled Water | 50.0 |
| | IGEPAL ® CO-630 (GAF) | 0.2 |
| | Laureth 23 | 1.9 |
| B. | Copolymer of Example I | 5.0 |
| C. | Distilled Water | 26.8 |
| | CHEELOX ® BF-13 (GAF) | 0.1 |

J. PERMANENT WAVE LOTION (continued)

| | Ingredients | % by Weight |
| --- | --- | --- |
| | Ammonium Thioglycolate, 60% | 11.3 |
| D. | Monoethanolamine, 99.9% | 4.7 |
| E. | Fragrance and Preservative | qs |

Part A was mixed in a glass mixing vessel at 70° C. until dissolved, after which the mixture was cooled to 25° C. and parts B through E added with mixing until homogeneous. Hair permed with this formulation was soft, lusterous and showed excellent combability with no damaging effect.

K. PERMANENT WAVE SOLUTION

| | Ingredients | % by Weight |
| --- | --- | --- |
| A. | Ammonium Thioglycolate (60%) | 12.0 |
| | Ammonium Hydroxide (28%) | 4.5 |
| | CHEELOX ® BF-13 (GAF) | 0.1 |
| | PEG-75 Lanolin (Solulan 75, Amerchol) | 0.5 |
| B. | Distilled Water | 77.9 |
| | Copolymer of Example I | 5.0 |

Ammonium thioglycolate and 80% of the total content of ammonium hydroxide were mixed after which CHEELOX ® BF-13 and PEG-75 lanolin were added with agitation. In separate container, distilled water and the copolymer of Example I were mixed until a solution was obtained whereupon the solution was added to part A. The resulting mixture was agitated until homogeneous and the pH was adjusted to 9.5 with ammonium hydroxide. Hair permed with this formulation produced the same results as in formulation J.

The copolymers of this invention have glossy film forming properties that support use in fixative products such as mousses and gels. The films are also clear and flexible so that curl retention is enhanced. Generally, for cosmetic and personal care uses, the polymers of this invention can be incorporated into standard preparations in a concentration of from about 0.05% to about 15% by weight of the total mixture.

WHAT IS CLAIMED IS:

1. The process for solution copolymerization, in an oxygen-free atmosphere of a quaternized amino acrylamide monomer having the formula:

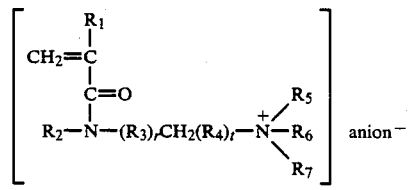

with a vinyl lactam monomer having the formula:

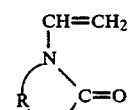

wherein R is alkylene having from 3 to 8 carbon atoms and is optionally substituted with lower alkyl; $R_1$ and $R_2$ are each independently hydrogen or methyl; $R_3$ and $R_4$ are each independently alkylene having from 1 to 18 carbon atoms which is optionally substituted with alkyl; the sum of r and t is 1 to 3; $R_5$ and $R_6$ are each independently lower alkyl; $R_7$ is hydrogen, alkyl, aralkyl or alkaryl having from 1 to 8 carbon atoms or an N-alkylene lactam radical having from 3 to 8 ring carbon atoms and the anion is an acidic anion which process comprises buffering the system before contacting said lactam and quaternized monomer with an aqueous solution containing between about 0.05 and about 0.5 weight % based on lactam of a buffer chelating agent having complexing properties having a pH greater than 5.5, contacting said monomers in the presence of continuous or incremental addition of an organic free radical initiator, controlling the pH of the system to above about 5.5 throughout the reaction and reacting said monomers under a continuous ebullition of nitrogen under conditions conducive to polymerization for a period of from about 1 to about 10 hours and recovering the quaternized copolymer of from about 2 to about 15 wt. % quaternized amino acrylamide, from about 85 to about 98 weight % vinyl lactam and less than 0.5 wt. % total unreacted monomer.

2. The process of claim 1 wherein said anion is selected from the group of halogen, tosylate, $SO_3$, $SO_4$, $HSO_4$, and $R_7SO_4$.

3. The process of claim 1 wherein the polymerization is carried out at a temperature of from about 30° C. to about 150° C. under a pressure of from about 20 mm Hg to about 50 psia for a period of from about 1 to about 10 hours.

4. The process of claim 3 wherein the polymerization is carried out at a temperature of from about 55° C. to about 75° C. under atmospheric pressure for a period of from about 2 to about 5 hours.

5. The process of claim 1 wherein said lactam monomer is N-vinyl pyrrolidone or N-vinyl caprolactam.

6. The process of claim 1 wherein $R_3$ and $R_4$ of said quaternized amino acrylamide monomer are each lower alkylene and $R_7$ of said quaternized amino acrylamide is hydrogen or lower alkyl.

7. The process of claim 6 wherein $R_1$ of said quaternized amino acrylamide monomer is methyl and the anion is chloride, said monomer is copolymerized with N-vinyl pyrrolidone or N-vinyl caprolactam and an organic peroxide initiator is gradually or incrementally introduced throughout the copolymerization reaction.

8. The process of claim 1 wherein between about 2% and about 15% by weight of said quaternized monomer is copolymerized with between about 98% and about 85% of said lactam.

9. The process of claim 1 wherein said buffer is an aqueous solution and is selected from the group of ethylene diamine tetraacid disodium salt, tetrasodium pyrophosphate, tribasic sodium phosphate, borax, calcium hydroxide, a mixture of anhydrous dibasic sodium phosphate and monobasic potassium phosphate, and a mixture of sodium carbonate and sodium bicarbonate.

10. The process of claim 6 wherein said buffer is an aqueous solution of tetrasodium pyrophosphate.

11. The process of claim 7 wherein said initiator is tertiary butyl peroxypivalate.

* * * * *